(12) United States Patent
Funazuka et al.

(10) Patent No.: US 9,789,480 B2
(45) Date of Patent: Oct. 17, 2017

(54) ASEPTIC MANIPULATION SYSTEM AND OBJECT-INTRODUCING METHOD FOR ASEPTIC MANIPULATION SYSTEM

(71) Applicant: SHIBUYA CORPORATION, Ishikawa (JP)

(72) Inventors: Takuya Funazuka, Ishikawa (JP); Masaharu Shomura, Ishikawa (JP)

(73) Assignee: SHIBUYA CORPORATION, ISHIKAWA (JP)

( * ) Notice: Subject to any disclaimer, the term of this patent is extended or adjusted under 35 U.S.C. 154(b) by 0 days.

(21) Appl. No.: 14/978,139

(22) Filed: Dec. 22, 2015

(65) Prior Publication Data

US 2016/0184814 A1    Jun. 30, 2016

(30) Foreign Application Priority Data

Dec. 25, 2014  (JP) ................. 2014-262748

(51) Int. Cl.
*B01L 1/04*    (2006.01)
*B25J 21/02*    (2006.01)
(Continued)

(52) U.S. Cl.
CPC ............. *B01L 1/04* (2013.01); *A61L 2/208* (2013.01); *A61L 2/24* (2013.01); *B25J 21/02* (2013.01);
(Continued)

(58) Field of Classification Search
CPC ............. B01L 1/04; B01L 2200/141; B01L 2200/145; A61L 2/24; A61L 2202/122; B25J 21/02; C12M 37/00; C12M 37/06
See application file for complete search history.

(56) References Cited

U.S. PATENT DOCUMENTS 2,244,082 A * 6/1941 Reyniers ............ B01L 1/04
119/417
4,262,091 A * 4/1981 Cox .................... B01L 1/04
435/253.6
(Continued)

FOREIGN PATENT DOCUMENTS

CN    202314527    7/2012
EP    2210618    7/2010
(Continued)

OTHER PUBLICATIONS

Search Report issued by European Patent Office (EPO) patent office in European Patent Office (EPO) Patent Application No. 15 200 790.2, dated Apr. 15, 2016.

*Primary Examiner* — Paul S Hyun
(74) *Attorney, Agent, or Firm* — Greenblum & Bernstein, P.L.C.

(57) ABSTRACT

An aseptic manipulation system comprises first and second operation chambers, an aseptic manipulation chamber, and a control unit. The control unit controls the ventilation of the first operation chamber for more than a first specified number of times, after an object is introduced into the first operation chamber, and ventilates the second operation chamber for more than a second specified number of times that is greater than the first specified number of times, after the object is transferred into the second operation chamber from the first chamber.

9 Claims, 4 Drawing Sheets

(51) Int. Cl.
  *A61L 2/20*   (2006.01)
  *A61L 2/24*   (2006.01)
  *C12M 1/12*   (2006.01)

(52) U.S. Cl.
  CPC ........ *C12M 37/00* (2013.01); *A61L 2202/122* (2013.01); *B01L 2200/02* (2013.01); *B01L 2200/025* (2013.01); *B01L 2200/141* (2013.01); *B01L 2200/145* (2013.01); *B01L 2300/048* (2013.01)

(56) References Cited

U.S. PATENT DOCUMENTS

| | | | |
|---|---|---|---|
| 2011/0053486 A1* | 3/2011 | Holtz | C12M 37/00 454/187 |
| 2011/0212513 A1 | 9/2011 | Yokoi et al. | |
| 2012/0040600 A1* | 2/2012 | Ortner | A41D 13/02 454/187 |
| 2013/0025221 A1* | 1/2013 | Mouzannar | E04H 3/08 52/234 |
| 2014/0137493 A1* | 5/2014 | Mouzannar | B01L 1/04 52/234 |
| 2014/0290162 A1 | 10/2014 | Tanimoto | |
| 2015/0192313 A1* | 7/2015 | Yokoi | B25J 21/02 454/187 |

FOREIGN PATENT DOCUMENTS

| | | |
|---|---|---|
| EP | 2363255 | 9/2011 |
| JP | 2014-198079 | 10/2014 |

* cited by examiner (5)

(6)

(7)

ASEPTIC MANIPULATION SYSTEM AND OBJECT-INTRODUCING METHOD FOR ASEPTIC MANIPULATION SYSTEM

BACKGROUND OF THE INVENTION

1. Field of the Invention

The present invention relates to an aseptic manipulation system having an isolator, in which an aseptic manipulation chamber is arranged, and a decontamination chamber for introducing an object into the aseptic manipulation chamber, and an object-introducing method for the aseptic manipulation system.

2. Description of the Related Art

Conventionally, there is known an aseptic manipulation system for performing regenerative medicine such as cell culture, which is disclosed in Japanese Unexamined Patent Publication No. 2014-198079. The aseptic manipulation system is arranged with two pass boxes in an early stage of an aseptic manipulation chamber, the inside of which is kept in an aseptic condition (corresponding to a grade A cleanliness level of air), and the pressures in the two pass boxes are enhanced stepwise towards the aseptic manipulation chamber so that the aseptic manipulation chamber can be installed in an environment of relatively low cleanliness level without a specific facility called a cell processing center (CPC), which is highly controlled in order to maintain a high level of cleanliness. Further, air-lock chambers are provided between the two pass boxes, between the subsequent pass box and the aseptic manipulation chamber, and between an external environment composed of a clean booth and the previous pass box, respectively, so that the environmental conditions between the two pass boxes, between the subsequent pass box and the aseptic manipulation chamber, and between the external environment the previous pass box are not in direct communication when introducing an object; and the object can be introduced into the aseptic manipulation chamber from the external environment while maintaining the aseptic condition.

In the above-described conventional aseptic manipulation system, air is prevented from flowing between the two pass boxes, between the subsequent pass box and the aseptic manipulation chamber, and between the external environment and the previous pass box, so that the cleanliness grade of the aseptic manipulation chamber is prevented from getting worse when introducing an object. However, the object needs to pass through the two pass boxes and the three air lock chambers, and thus, the introducing operations are cumbersome. Further, every time the air-lock chambers are opened to a space of a relatively low grade air a small amount of air flows into the air-lock chambers, which can lower the cleanliness thereof, and if the frequency of the opening operation of the air lock chambers becomes high, it would become difficult to maintain the cleanliness of each of the pass boxes.

SUMMARY OF THE INVENTION

An object of the present invention is to always maintain the aseptic manipulation chamber at a desired cleanliness grade, even in an environment that is not highly controlled, such as a cell-processing center (CPC).

According to the present invention, an aseptic manipulation system comprises an aseptic manipulation chamber, the inside of which is kept in an aseptic condition, a decontamination chamber, a first ventilation mechanism, a second ventilation mechanism, and a control unit. The decontamination chamber, which is provided for removing microbes adhering to an object introduced into the aseptic manipulation chamber from the outside thereof, has a first operation chamber provided with an inlet portion that can be closed, a second operation chamber connected to the first operation chamber and provided with an outlet portion that can be closed, a communication portion communicating between the first chamber and the second chamber and being able to close, an inlet portion closing mechanism for closing the inlet portion, an outlet portion closing mechanism for closing the outlet portion, and a communication portion closing mechanism for closing the communication portion. The first ventilation mechanism ventilates the inside of the first operation chamber, and the second ventilation mechanism ventilates the inside of the second operation chamber. The control unit monitors the open-closed states of the inlet portion closing mechanism, the outlet portion closing mechanism, and the communication portion closing mechanism, and controls the operations of the first ventilation mechanism and the second ventilation mechanism. The control unit ventilates the inside of the first operation chamber with the first ventilation mechanism for more than a first specified number of times after an object is introduced into the first operation chamber from the outside and the inlet portion is closed while the communication portion is closed. The control unit ventilates the inside of the second operation chamber with the second ventilation mechanism for more than a second specified number of times, which is greater than the first specified number of times, after the object is transferred into the second operation chamber from the first chamber and the communication portion is closed while the outlet portion is closed.

A method for introducing an object according to the present invention is provided for introducing an object into an aseptic manipulation system comprising an aseptic manipulation chamber, the inside of which is kept in an aseptic condition, a decontamination chamber, a first ventilation mechanism, and a second ventilation mechanism. The decontamination chamber is provided for removing microbes adhering to an object introduced into the aseptic manipulation chamber from the outside thereof, and has a first operation chamber provided with an inlet portion that can be closed, a second operation chamber connected to the first operation chamber and provided with an outlet portion that can be closed, and a communication portion communicating between the first chamber and the second chamber and being able to close. The first ventilation mechanism ventilates the inside of the first operation chamber, and the second ventilation mechanism ventilates the inside of the second operation chamber. The object-introducing method comprises the steps of opening the inlet portion while the communication portion is closed and ventilating the first operation chamber with the first ventilation mechanism for more than a first specified number of times after introducing the object into the first operation chamber from the outside and closing the inlet portion; opening the communication portion while closing the outlet portion, and ventilating the second operation chamber with the second ventilation mechanism for more than a second specified number of times that is greater than the first specified number of times after transferring the object from the first operation chamber to the second operation chamber and closing the communication portion; decontaminating the object in at least one of the first operation chamber and the second operation chamber, which is being ventilated; and opening the outlet portion to transfer the object from the second operation chamber to the aseptic manipulation chamber.

BRIEF DESCRIPTION OF THE DRAWINGS

The object and advantages of the present invention will be better understood from the following description, with reference to the accompanying drawings in which.

DESCRIPTION OF THE PREFERRED EMBODIMENTS

Figure 1:
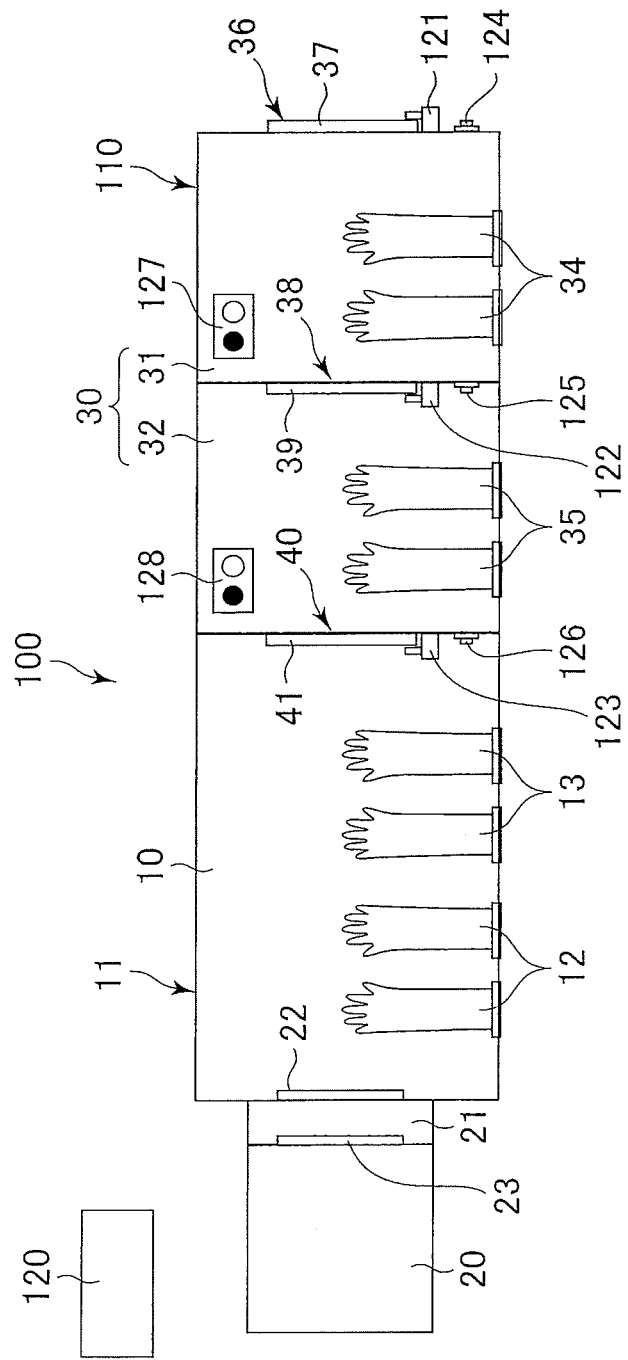
FIG. 1 is a view showing components of an aseptic manipulation system to which an embodiment of the present invention is applied.

In the following, an aseptic manipulation system 100, which is an embodiment of the present invention, will be described with a first embodiment which is illustrated in the drawings. FIG. 1 shows a general structure of the aseptic manipulation system 100. The aseptic manipulation system 100 includes an isolator 11 with an aseptic manipulation chamber 10 formed therein, a pass box 110, and a control unit 120. The inside of the aseptic manipulation chamber 10 is maintained in an aseptic condition. The pass box 110 is connected to an inlet portion of the aseptic manipulation chamber 10. A decontamination chamber 30 is configured in the pass box 110 to remove microbes adhering to an object introduced into the aseptic manipulation chamber 10 from the outside of the aseptic manipulation system 100. The control unit 120 controls ventilating operations of the isolator 11 and the pass box 110, and monitors open-closed states of the inlet portion and the outlet portion of the pass box 110, as described later.

The aseptic manipulation system 100 is installed in a grade D cleanliness environment of air. According to the "Guidelines relating to the manufacture of aseptic pharmaceutical products using an aseptic manipulation" issued by the Ministry of Health, Labor and Welfare Japan, the grade D cleanliness environment is a cleanliness level in which the number of floating particulates having a diameter of greater than or equal to 0.5 μm is less than or equal to 3,520,000 per 1 $m^3$ of air in a non-operating condition. On the other hand, the cleanliness level of air in the aseptic manipulation chamber 10 is required to be grade A. The grade A cleanliness environment is a cleanliness level in which the number of floating particulates having a diameter of greater than or equal to 0.5 μm is less than or equal to 3,520 per 1 $m^3$ of air in both an operating condition and a non-operating condition. This corresponds to class 5 in ISO, and class 100 in the guidelines of the USA.

The decontamination chamber 30 is divided into a first operation chamber 31 and a second operation chamber 32. An incubator 20 for cultivating human cells can be attached to or detached from the aseptic manipulation chamber 10 on the side opposite to the decontamination chamber 30. Note that the first operation chamber 31 and the second operation chamber 32 may be defined by dividing the inside of the single pass box 110, or may be formed by connecting two independent pass boxes 110.

In this embodiment, the cleanliness of each of the operation chambers 31 and 32 is controlled in such a manner that the cleanliness of air in the second operation chamber 32 is set to a grade B, which can be communicated with a grade A cleanliness environment, and the cleanliness of air in the first operation chamber 31 is set to a grade C, which can be communicated with a grade B cleanliness environment. The grade B cleanliness environment is a cleanliness level in which the number of floating particulates having a diameter of greater than or equal to 0.5 μm per 1 $m^3$ of air is less than or equal to 352,000 in an operating condition, and is less than or equal to 3,520 in a non-operating condition. This corresponds to class 7 in ISO (a standard for an operating condition), and class 10,000 in the guidelines of the USA. When the second operation chamber 32 is communicated with the aseptic manipulation chamber 10 with a grade A cleanliness environment, the cleanliness of air in the second operation chamber 32 is set to a grade B cleanliness environment for a non-operating condition. On the other hand, the grade C cleanliness environment is a cleanliness level in which the number of floating particulates having a diameter of greater than or equal to 0.5 μm per 1 $m^3$ of air is less than or equal to 3,520,000 in an operating condition, and is less than or equal to 352,000 in a non-operating condition. This corresponds to class 8 in ISO (a standard for an operating condition), and class 100,000 in the guidelines of the USA. When the first operation chamber 31 is communicated with the second operation chamber 32 with a grade B cleanliness environment, the cleanliness of air in the first operation chamber 31 is set to a grade C cleanliness environment for a non-operating condition.

Gloves 12 and 13 are provided on a wall of the aseptic manipulation chamber 10 in order to perform various kinds of treatments on an object placed in the aseptic manipulation chamber 10 from the outside of the aseptic manipulation chamber 10. Similarly, gloves 34 and 35 are provided in the first operation chamber 31 and the second operation chamber 32 of the decontamination chamber 30.

The first operation chamber 31 is located on an opposite side of the aseptic manipulation chamber 10 with respect to the second operation chamber 32, and an inlet portion 36 of the first operation chamber 31 can be closed by a first closing member (an inlet portion closing mechanism) 37. The second operation chamber 32 is connected to the first operation chamber 31, and a communication portion 38 communicating between the first operation chamber 31 and the second operation chamber 32 can be closed by a second closing member (a communication portion closing mechanism) 39. An outlet portion 40 of the second operation chamber 32, or a connecting portion to the aseptic manipulation chamber 10 can be closed by a third closing member (an outlet portion closing mechanism) 41. In this embodiment, the first, second, and third closing members 37, 39, and 41 are opened and closed by hand, and these open-closed states are monitored by the control unit 120.

The first, second, and third closing members 37, 39, and 41 can be locked by locking mechanisms 121, 122, and 123 controlled by the control unit 120, and can be set to the locked state or the released state by pressing open-close button 124, 125, or 126. The first operation chamber 31 and the second operation chamber 32 are provided with signals 127 and 128, which indicate that the number of ventilation cycles has reached a specified number of times and the ventilation of the first or second operation chamber 31 or 32 has ended. The lighting states of the signals 127 and 128 are controlled by the control unit 120, and changed depending upon the ventilation conditions of the first and second operation chambers 31 and 32, as described later.

The pressure relationships among the aseptic manipulation chamber 10, the first operation chamber 31, and the second operation chamber 32 are controlled in this embodiment in such a manner that the air pressure in the first operation chamber 31 is higher than the ambient pressure, the air pressure in the second operation chamber 32 is lower than that of the first operation chamber 31, the air pressure in the aseptic manipulation chamber 10 is higher than that of the first operation chamber 31, and all of the pressures are positive in comparison with the ambient pressure. Thus, the air pressure in the second operation chamber 32 is kept lower than the first operation chamber 31 and the aseptic manipulation chamber 10 so that the air is prevented from flowing between the first operation chamber 31 and the aseptic manipulation chamber 10. Due to this, even if the aseptic manipulation chamber 10 and the first operation chamber 31 are communicating with each other, the ambient air contaminated by the ambient environment is prevented from flowing into the aseptic manipulation chamber 10, and pathogens such as viruses are prevented from flowing out from the aseptic manipulation chamber 10 to the ambient environment.

When the incubator 20 is attached to the aseptic manipulation system 100, the incubator 20 is connected to the aseptic manipulation chamber 20 through a connecting portion 21. A partition wall between the aseptic manipulation chamber 10 and the connecting portion 21 is opened and closed by a first open-close member 22, and a portion between the connecting portion 21 and the incubator 20 is opened and closed by a second open-close member 23 provided in the incubator 23.

Figure 2:
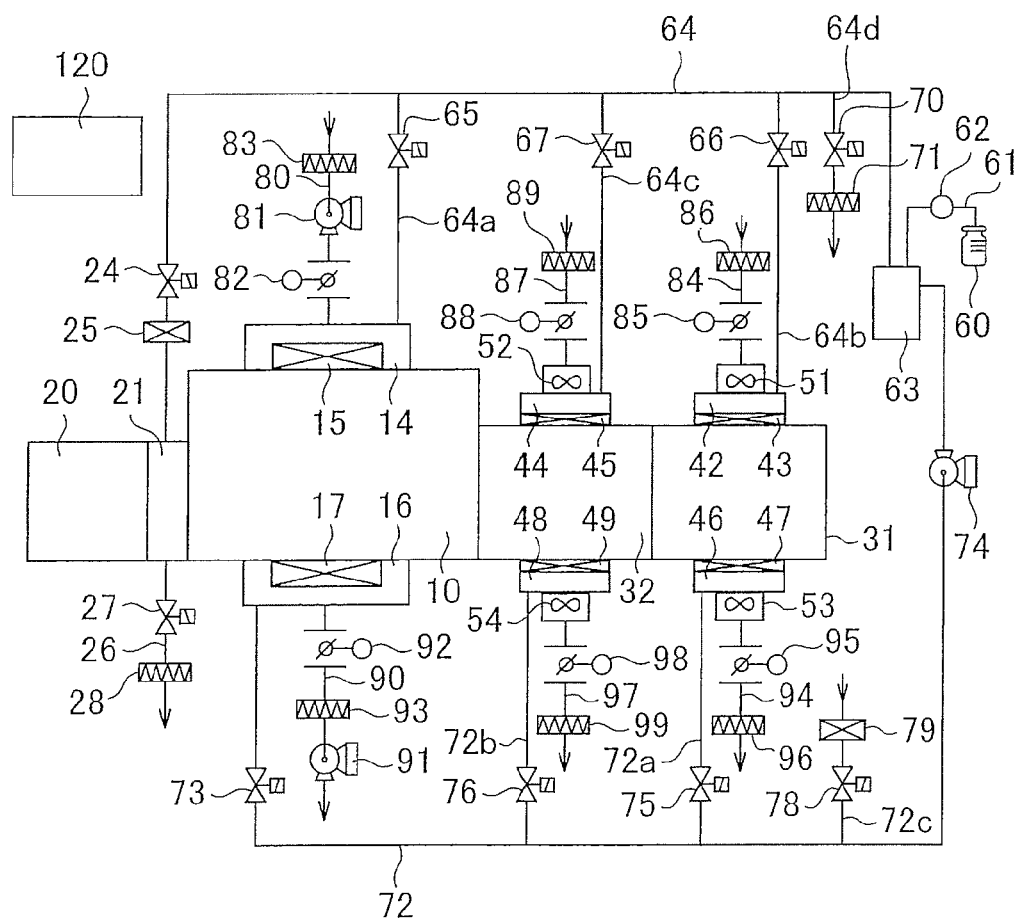
FIG. 2 is a diagram showing a fluid supply circuit for supplying and discharging decontamination gas and clean air in the aseptic manipulation system shown in FIG. 1.
Figure 3:
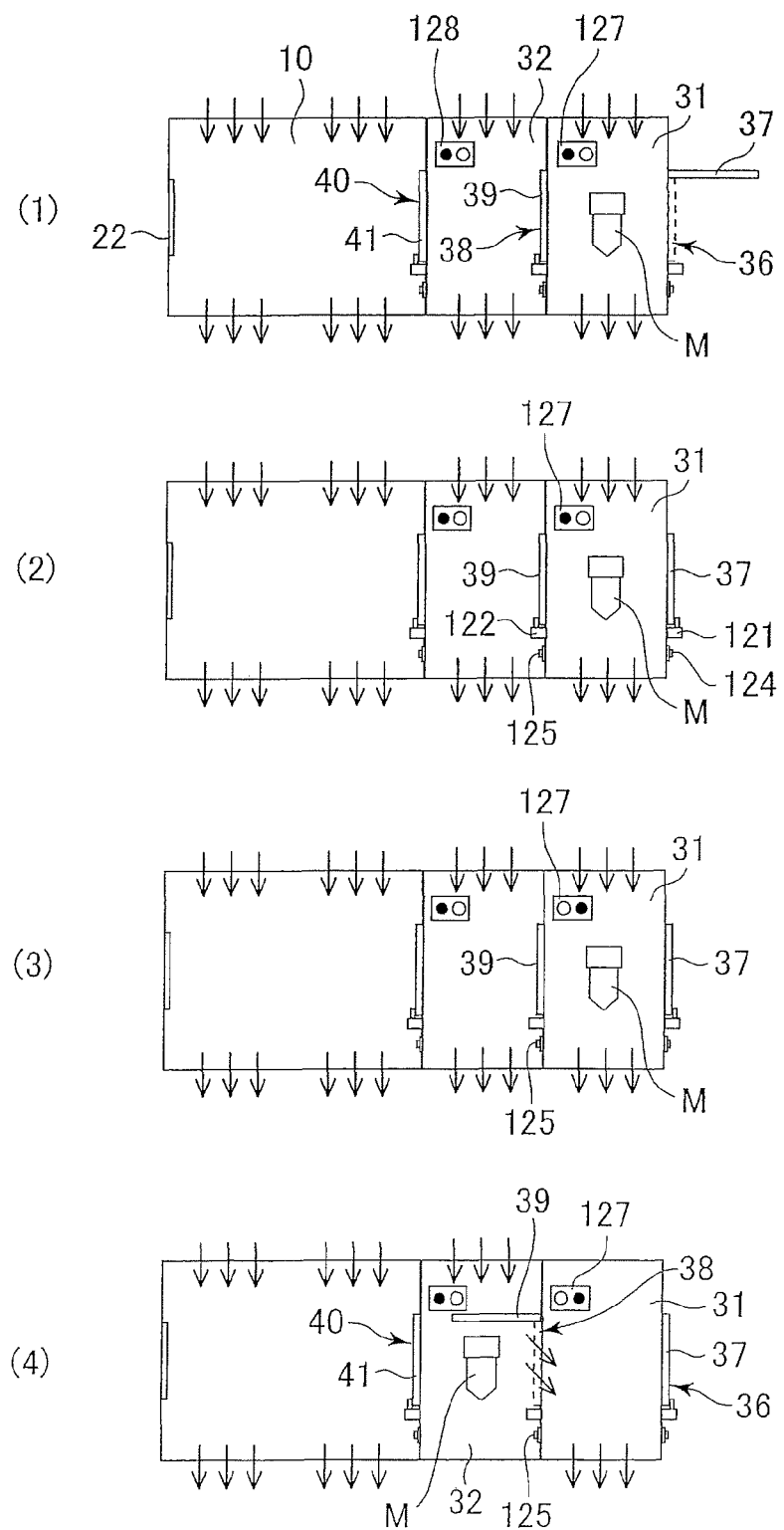
FIG. 3 is a diagram showing the operations of steps (1)-(4) of the aseptic manipulation system shown in FIG. 1.
Figure 4:
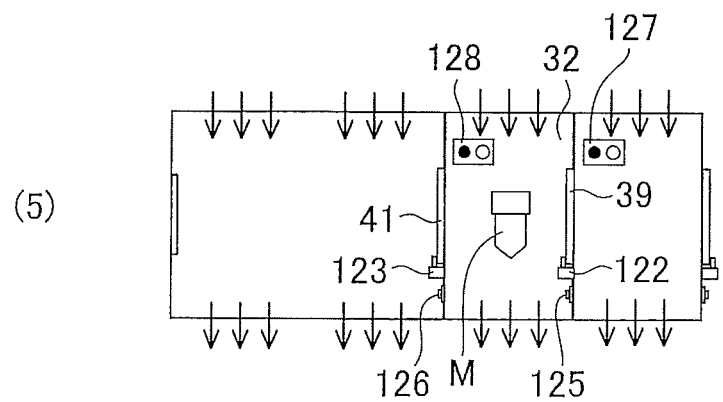
FIG. 4 is a diagram showing the operations of steps (5)-(7) of the aseptic manipulation system shown in FIG. 1.
Figure 4:
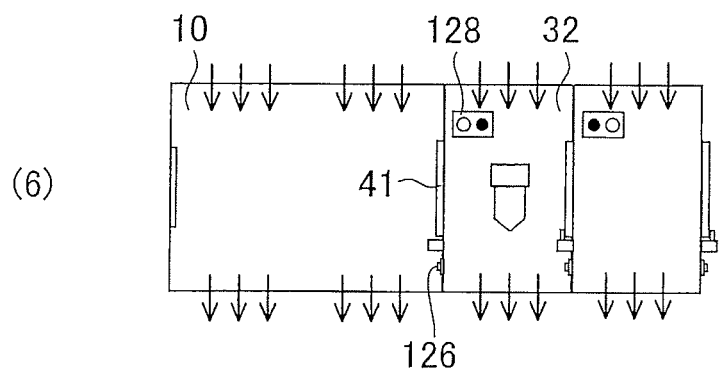
Figure 4:
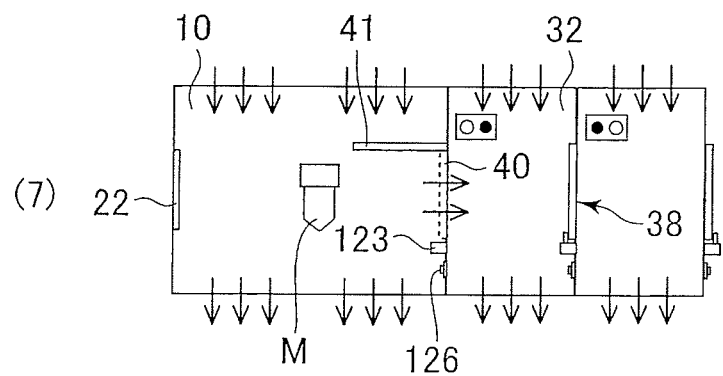

FIG. 2 illustrates the construction of a decontamination gas supply device, which supplies decontamination gas (decontamination vapor) to the aseptic manipulation chamber 10, the first operation chamber 31, the second operation chamber 32, and the connecting portion 21. In this embodiment, the decontamination gas is hydrogen peroxide vapor, and hydrogen peroxide aqueous solution is stored in a bottle 60. The hydrogen peroxide aqueous solution is supplied from the bottle 60 to an evaporator 63 in a predetermined quantity by a pump 62, which is provided in a decontamination medium supply passage 61, and is heated by the evaporator 63 to form hydrogen peroxide vapor. A circulation passage 72 is connected to an inlet of the evaporator 63, and hydrogen peroxide that is generated is discharged from the evaporator 63 by an operation of a circulation blower 74 provided in the circulation passage 72. A decontamination gas supply passage 64 connected to an outlet of the evaporator 63 is connected to the aseptic manipulation chamber 10, the first operation chamber 31, and the second operation chamber 32 through open-close valves 65, 66, and 67.

A gas supply chamber 14 is provided on a top side of the aseptic manipulation chamber 10, and a first branch passage 64a of the decontamination gas supply passage 64 is connected to the gas supply chamber 14. A HEPA filter 15 is arranged in the gas supply chamber 14, and hydrogen peroxide vapor supplied to the gas supply chamber 14 is supplied to the aseptic manipulation chamber 10 through the HEPA filter 15.

Similarly, a gas supply chamber 42 is provided on a top side of the first operation chamber 31, and a second branch passage 64b of the decontamination gas supply passage 64 is connected to the gas supply chamber 42. A HEPA filter 43 is arranged in the gas supply chamber 42, and hydrogen peroxide vapor supplied to the gas supply chamber 42 is supplied to the first operation chamber 31 through the HEPA filter 43. Regarding the second operation chamber 32 as well, hydrogen peroxide vapor is supplied from a third branch passage 64c of the decontamination gas supply passage 64 to a gas supply chamber 44, and supplied to the second operation chamber 32 through a HEPA filter 45.

The connecting portion 21 is connected to the decontamination gas supply passage 64 through an open-close valve 24 and a HEPA filter 25. Namely, hydrogen peroxide vapor passing through the decontamination gas supply passage 64 is supplied to the connecting portion through the HEPA filter 25.

A pressure-adjusting valve 70 is provided in a fourth branch passage 64d of the decontamination gas supply passage 64. The pressure-adjusting valve 70 is arranged on a downstream side of the circulation blower 74 so that when the circulation blower 74 is operated, gas is discharged from the decontamination gas supply passage 64 to reduce the amount of gas supply in the passage 64; and the pressures are adjusted lower in the aseptic manipulation chamber 10, the first operation chamber 31, and the second operation chamber 32. Note that a catalyst 71 is arranged in an open end of the fourth branch passage 64d to prevent the outflow of a toxic substance outside of the aseptic manipulation system 100.

A gas discharge chamber 16 is provided on a bottom side of the aseptic manipulation chamber 10, and a HEPA filter 17 is arranged in the gas discharge chamber 16. The gas discharge chamber 16 is connected to the circulation passage 72, which is provided with an open-close valve 73 and connected to the inlet of the evaporator 63. Therefore, gas in the aseptic manipulation chamber 10 is discharged into the gas discharge chamber 16 through the HEPA filter 17 by a discharge operation of the circulation blower 74, and flows back to the evaporator 63 through the circulation passage 72.

Similarly, a HEPA filter 47 is arranged in a gas discharge chamber 46 formed on a bottom side of the first operation chamber 31, and a HEPA filter 49 is arranged in a gas discharge chamber 48 formed on a bottom side of the second operation chamber 32. The gas discharge chambers 46 and 48 are connected to first and second branch passages 72a and 72b of the circulation passage 72, in which open-close valves 75 and 76 are provided. Therefore, gas in the first operation chamber 31 and the second operation chamber 32 is discharged into the gas discharge chambers 46 and 48 through the HEPA filters 47 and 49, and flows back to the evaporator 63 through the circulation passage 72.

A pressure-adjusting valve 78 is provided in a third branch passage 72c of the circulation passage 72. The pressure-adjusting valve 78 is arranged on an upstream side of the circulation blower 74 so that when the circulation blower 74 is operated, gas flows into the circulation passage 72 to increase the amount of gas supply in the passage 72, and the pressures are adjusted higher in the aseptic manipulation chamber 10, the first operation chamber 31, and the second operation chamber 32. An open end of the third branch passage 72c is open to the outside of the aseptic manipulation system 100 through the HEPA filter 79.

A structure for supplying clean gas into the aseptic manipulation chamber 10, the first operation chamber 31 and the second operation chamber 32 is described below. A first gas supply passage 80 is connected to the gas supply chamber 14 of the aseptic manipulation chamber 10. An air supply blower 81 is provided in the first gas supply passage 80, and an air volume regulating valve 82 is provided between the air supply blower 81 and the gas supply chamber 14. A catalyst 83 is provided in an open end of the first air supply passage 80.

According to the construction described above, by opening the air volume regulating valve 82 and operating the air supply blower 81, air flows into the gas supply chamber 14 from the outside through the first gas supply passage 80, and is purified by the HEPA filter 15 and supplied into the aseptic manipulation chamber 10. Further, by adjusting the opening degree of the air volume regulating valve 82 or the air flow volume of the air supply blower 81, the volume of air supplied to the aseptic manipulation chamber 10 can be increased or decreased.

An air supply fan 51 is provided for the gas supply chamber 42 of the first operation chamber 31, and a second gas supply passage 84 is connected to the air supply fan 51. An air volume regulating valve 85 is provided in the second gas supply passage 84, and a catalyst 86 is provided in an open end of the second gas supply passage 84. Similarly, an air supply fan 52 is provided for the gas supply chamber 44 of the second operation chamber 32, and a third gas supply passage 87 is connected to the air supply fan 52. An air volume regulating valve 88 is provided in the third gas supply passage 87, and a catalyst 89 is provided in an open end of the third gas supply passage 87.

According to the construction described above, by opening the air volume regulating valve 85 and operating the air supply fan 51, air flows into the gas supply chamber 42 from the outside through the second gas supply passage 84, and is purified by the HEPA filter 43 and supplied into the first operation chamber 31. Further, by adjusting the opening degree of the air volume regulating valve 85 or the air flow volume of the air supply fan 51, the volume of air supplied to the first operation chamber 31 can be increased or decreased. Similarly, by opening the air volume regulating valve 88 and operating the air supply fan 52, air flows into the gas supply chamber 44 from the outside through the third gas supply passage 87, and is purified by the HEPA filter 45 and supplied into the second operation chamber 32. Further, by adjusting the opening degree of the air volume regulating valve 88 or the air flow volume of the air supply fan 52, the volume of air supplied to the second operation chamber 32 can be increased or decreased.

A structure for discharging gas from the aseptic manipulation chamber 10, the first operation chamber 31, the second operation chamber 32, and the connecting portion 21 is described below. A first gas discharge passage 90 is connected to the gas discharge chamber 16 of the aseptic manipulation chamber 10, and an air discharge blower 91 is provided in the first gas discharge passage 90. An air volume regulating valve 92 and a catalyst 93 are provided between the air discharge blower 91 and the gas discharge chamber 16.

According to the construction described above, by opening the air volume regulating valve 92 and operating the air discharge blower 91, air passing through the HEPA filter 17 and the air discharge chamber 16 from the aseptic manipulation chamber 10 is discharged outside through the first gas discharge passage 90. Further, by adjusting the opening degree of the air volume regulating valve 92 or the air flow volume of the air discharge blower 91, the volume of air discharged from the aseptic manipulation chamber 10 can be increased or decreased.

An air discharge fan 53 is provided for the gas discharge chamber 46 of the first operation chamber 31, and a second gas discharge passage 94 is connected to the air discharge fan 53. An air volume regulating valve 95 and a catalyst 96 are provided in the second gas discharge passage 94. Similarly, an air discharge fan 54 is provided for the gas discharge chamber 48 of the second operation chamber 32, and a third gas discharge passage 97 is connected to the air discharge fan 54. An air volume regulating valve 98 and a catalyst 99 are provided in the third gas discharge passage 97.

According to the construction described above, by opening the air volume regulating valve 95 and operating the air discharge fan 53, air passing through the HEPA filter 47 and the air discharge chamber 46 from the first operation chamber 31 is discharged outside through the second gas discharge passage 94. Further, by adjusting the opening degree of the air volume regulating valve 95 or the air flow volume of the air discharge fan 53, the volume of air discharged from the first operation chamber 31 can be increased or decreased. Similarly, by opening the air volume regulating valve 98 and operating the air discharge fan 54, air passing through the HEPA filter 49 and the air discharge chamber 48 from the second operation chamber 32 is discharged outside through the third gas discharge passage 97. Further, by adjusting the opening degree of the air volume regulating valve 98 or the air flow volume of the air discharge fan 54, the volume of air discharged from the second operation chamber 32 can be increased or decreased.

As described above, the inside of the first operation chamber 31 is ventilated by operations of the air volume regulating valve 85, the air supply fan 51, the air discharge fan 53, and the air volume regulating valve 95, which constitute the first ventilation mechanism. The inside of the second operation chamber 32 is ventilated by operations of the air volume regulating valve 88, the air supply fan 52, the air discharge fan 54, and the air volume regulating valve 98, which constitute the second ventilation mechanism. The inside of the aseptic manipulation chamber 10 is ventilated by operations of the air volume regulating valve 82, the air supply blower 81, the air discharge blower 91, and the air volume regulating valve 92, which constitute the third ventilation mechanism. On the other hand, by increasing or decreasing the volume of air supplied to or the volume of air discharged from the aseptic manipulation chamber 10, the first operation chamber 31, and the second operation chamber 32, it is possible to adjust the pressure in each of the aseptic manipulation chamber 10, the first operation chamber 31, and the second operation chamber 32. This pressure adjustment is performed by the control unit 120, which can maintain the pressure in each of the chambers within a predetermined range, and maintain the pressure relationship among the chambers at a predetermined condition.

The control unit 120 controls the operations of the first, second, and third ventilation mechanisms to ventilate the first operation chamber 31 with a number of ventilations that is more than a first specified number of times such that the inside of the first operation chamber 31 becomes a grade C cleanliness environment in a non-operating condition, which can be communicated with a grade B cleanliness environment; and to ventilate the second operation chamber 32 with a number of ventilations that is more than a second specified number of times such that the inside of the second operation chamber 32 becomes a grade B cleanliness environment in a non-operating condition, which can be communicated with a grade A cleanliness environment. On the other hand, the aseptic manipulation chamber 10 is ventilated so that a grade A cleanliness environment can be maintained.

The number of ventilations (N) indicates how many times aeration can be carried out per one hour for the space subjected to the aeration. The number of ventilations is obtained by dividing the air flow volume for ventilation (F) by the volume of the space (R):

$$N = (F \text{ m}^3/\text{minute} \times 60 \text{ minutes})/R \text{ m}^3$$

Note that a standard for the number of ventilations for each of the grades is as follows: the number for a grade A is more than or equal to 300, the number for a grade B is more than or equal to 300 in a non-operating condition and more than or equal to 40 in an operating condition, and the number for grade C is more than or equal to 40 in a non-operating condition and more than or equal to 20 in an operating condition. According to these standards, the second specified number of times is more than or equal to 300, and the first specified number of times is more than or equal to 40. An actual number of times may be determined while considering the result of a measurement of the number of floating particulates remaining in the space, for example. In an actual application, the number of ventilations is controlled by using the operation time instead of the number of times. Namely, in the embodiment, the control unit 120 obtains a time, in which ventilations are performed for a required number of times, to determine a ventilation time, and maintains the closed conditions of the first operation chamber 31 and the second operation chamber 32 until reaching the ventilation time. In this case, since the ventilation time is changed depending upon the air flow volume for ventilation and the volume of the space, the ventilation time for the second operation chamber is not necessarily longer than that of the first operation chamber 31.

A gas discharge passage 26 is connected to the decontamination gas supply passage 64 on the side opposite to the connecting portion 21. An open-close valve 27 is provided in the gas discharge passage 26, and a catalyst 28 is arranged in an open end of the gas discharge passage 26.

With reference to FIGS. 1-4, the following section describes an operation in a ventilation mode of the embodiment. Note that the incubator 20 and the connecting portion 21 are omitted in FIGS. 3 and 4.

Before starting the ventilation mode, each of the aseptic manipulation chamber 10, the first operation chamber 31, and the second operation chamber 32 is supplied with hydrogen peroxide vapor, and aeration is carried out for the purpose of decontamination. When the decontamination using hydrogen peroxide vapor has been performed for a predetermined time, the pump 62 and the circulation blower 74 are stopped, and the valves 24, 27, 65, 66, 67, 70, 73, 75, 76, and 78 are closed to stop the supply of hydrogen peroxide vapor. On the other hand, the air supply and the air discharge for the aseptic manipulation chamber 10, the first operation chamber 31, and the second operation chamber 32 are continuously carried out so that the inside of each of the chambers is maintained in an aseptic condition by keeping the inside pressure positive relative to the external environment, with the highest pressure maintained in the aseptic manipulation chamber 10 and the second highest pressure maintained in the first operation chamber 31.

In step (1), the first closing member 37 is opened, and an object M to be subjected to a treatment in the aseptic manipulation chamber 10 is placed in the first operation chamber 31 through the inlet portion 36. The second closing member 39 is closed, so that the second operation chamber 32 does not communicate with the external environment.

In step (2), the first closing member 37 is closed and set to a locked state by the locking mechanism 121 by pressing the open-close button 124, so that the first operation chamber 31 is hermetically isolated from the outside. The control unit 120 maintains a locked closed state, in which the locking mechanisms 121 and 122 cannot be released even if the open-close buttons 124 and 125 are depressed. In this state, the air volume regulating valve 85, the air supply fan 51, the air discharge fan 53, and the air volume regulating valve 95, which constitute the first ventilation mechanism, are controlled by the control unit 120 and the first operation chamber 31 is ventilated for a first ventilation time, which has been predetermined. Although the inside of the first operation chamber 31 is originally set to a grade C cleanliness environment, the cleanliness level of the first operation chamber 31 is assumed to decline to a grade D because of the communication with the external environment. However, the first operation chamber 31 is ventilated for more than a first specified number of times, which has been checked and determined beforehand, and the cleanliness level of the first operation chamber 31 is instead maintained at grade C, which can be communicated with a grade B cleanliness environment in the next process.

While the first operation chamber 31 is ventilated, an operator's hands are inserted in the gloves 34 to wipe the object M with a nonwoven fabric soaked in alcohol, which is a decontaminant, to remove microbes adhering to the object M. For the first ventilation time, the first operation chamber 31 must be completely isolated from the outside; even if the wiping-off operation of the object M by the operator has been completed, the second closing member 39 should not be opened. Therefore, in this embodiment, for the first ventilation time, the signal 127 is set to a lighting state by the control unit 120 to indicate that the second closing member 39 should be maintained in the closed state.

After the first ventilation time has passed, since the inside of the first operation chamber 31 returns to a grade C cleanliness environment (a non-operation condition), the process proceeds to step (3) and the signal 127 is changed to a lighting state to indicate that the second closing member 39 can be opened. In this state, the locked state of the second closing member 39 held by the locking mechanism 122 can be released by pressing the open-close button 125. Note that as an informing mechanism indicating the completion of ventilation of the first operation chamber 31, an auditory device such as a buzzer, and a physical sensory device such as a vibrator, can be utilized instead of a visual device such as a character indicator or a signal like the one used in the embodiment.

Then, in step (4), an operator's hands are inserted in the gloves 35 to press the open-close button 125 to release the second closing member 39, and the object M is then transferred from the first operation chamber 31 to the second operation chamber 32 through the communication portion 38. The transfer of the object M is carried out while the communication portion 38 is open to allow communication between the first operation chamber 31 and the second operation chamber 32, while maintaining the closed states of the inlet portion 36 and the outlet portion 40. Immediately before the transfer, in the second operation chamber 32 the air volume regulating valves 88 and 98, which constitute the second ventilation mechanism, are opened by a predetermined opening degree, the air supply fan 52 and the air discharge fan 54 are operated with a predetermined air volume, and thus, the inside pressure of the second operation chamber 32 is maintained at a positive pressure lower than that of the first operation chamber 31 to preserve a grade B cleanliness environment in the second operation chamber 32, while the first operation chamber 31 is continuously ventilated by the first ventilation mechanism and maintained at a grade C cleanliness environment. In this embodiment, with the opening operation of the second closing member 39, the air volume regulating valves 85 and 98 are closed, the air supply fan 51 and the air discharge fan 54 are stopped, and the air supply volume controlled by the air volume regulating valve 88 and the air supply fan 52 is adjusted to be greater than the air discharge volume controlled by the air volume regulating valve 95 and the air discharge fan 53.

Therefore, when the second closing member 39 is open, it generates a strong current of air that flows from an upper portion of the second operation chamber 32 to a lower portion of the first operation chamber 31, so that the atmosphere in the first operation chamber 31 is prevented from flowing into the second operation chamber 32. Note that, in step (4), the positive pressure conditions of the first operation chamber 31 and the second operation chamber 32 relative to the external environment are maintained.

As another example for generating a current flowing from the second operation chamber 32 to the first operation chamber 31, all of the air supply fans 51 and 52 and the air discharge fans 53 and 54 may be operated, and the air volume regulating valves 85 and 98 may be opened by a relatively small opening degree. That is to say, if the air supply volume for the second operation chamber 32 is greater than that for the first operation chamber 31 while the air discharge volume for the first operation chamber 31 is greater than that for the second operation chamber 32, the pressure in the second operation chamber 32 becomes higher than that in the first operation chamber 31 and generates a current flowing from the second operation chamber 32 to the first operation chamber 31. Note, it is possible to control the operation environment in such a manner that the pressure in the second operation chamber 32 is always higher than that in the first operation chamber 31 and lower than that in the aseptic manipulation chamber 10, and the pressures in all of these chambers are positive relative to the external environment.

In step (5), the second closing member 39 is closed by the operator' hands inserted in the gloves 35. The open-close button 125 is then depressed by the operator to set the second closing member 39 to a locked state with the locking mechanism 122 so that the second operation chamber 32 is hermetically isolated from the first operation chamber 31. When the locking mechanisms 122 and 123 are operated, the control unit 120 sets a locked closed state, in which the locking mechanisms 121 and 122 cannot be released even if the open-close buttons 124 and 125 are depressed. In this state, the air volume regulating valve 88, the air supply fan 52, the air discharge fan 54, and the air volume regulating valve 98, which constitute the second ventilation mechanism, are controlled by the control unit 120 and the second operation chamber 32 is ventilated for the second ventilation time, which has been predetermined. Although the second operation chamber 32 was in a grade B cleanliness environment until step (3), the cleanliness level of the second operation chamber 32 is assumed to decline to a grade C because of the opening of the second closing member 39 in step (4). The second ventilation time is set similar to the way the first ventilation time is determined so that the inside of the second operation chamber 32 must return to a grade B cleanliness environment. Namely, the second operation chamber 32 is ventilated for more than the second specified number of times that is greater than the first specified number of times to attain the grade B cleanliness level of the second operation chamber 32, which can be communicated with a grade A cleanliness environment in the next process.

While the second operation chamber 31 is ventilated, the operator's hands are inserted in the gloves 35 to wipe the object M with a nonwoven fabric soaked in oxydol (i.e., hydrogen peroxide solution), which is a decontaminant, to remove microbes adhering to the object M. Thus, different decontaminants are used in the first decontamination operation in the first operation chamber 31 and the second decontamination operation in the second operation chamber 32 so that it is possible to remove all sorts of microbes, bacteria, and viruses that have different resistances from each other. Note that, as the decontamination medium used in the first and second decontamination operations in the ventilation mode, general antiseptic solutions or germicides such as alcohol (i.e., ethanol for disinfection), oxydol (i.e., hydrogen peroxide solution), peracetic acid, and sodium hypochlorite, which are liquid at normal temperature, can be used. While the second ventilation is carried out, the second closing member 32 must be completely isolated from the first operation chamber 31 and the aseptic manipulation chamber 10. Therefore, in the embodiment, for the second ventilation time, the signal 128 is set to a lighting state by the control unit 120 to indicate that the third closing member 41 should be maintained in the closed state.

When the second ventilation time has passed, since the inside of the second operation chamber 32 returns to a grade B cleanliness environment (a non-operation condition), the process proceeds to step (6), and the signal 128 is changed to a lighting state to indicate that the third closing member 41 can be opened.

Then, in step (7), the operator's hands are inserted in the gloves 13 to press the open-close button 126 to release the third closing member 41, and the object M is then transferred from the second operation chamber 32 to the aseptic manipulation chamber 10 through the outlet portion 40. The transfer of the object M is carried out while the outlet portion 40 is open for communication between the second operation chamber 32 and the aseptic manipulation chamber 10, while maintaining the closed states of the communication portion 38 and the first open-close member 22. Immediately before the transfer, in the aseptic manipulation chamber 10 the air volume regulating valves 82 and 92, which constitute the third ventilation mechanism, are opened by a predetermined opening degree and the air supply blower 81 and the air discharge blower 91 are operated with a predetermined air volume so that the inside pressure of the aseptic manipulation chamber 10 is maintained at a positive pressure higher than that of the second operation chamber 32 to preserve a grade A cleanliness environment in the aseptic manipulation chamber 10, while the second operation chamber 32 is continuously ventilated by the second ventilation mechanism to preserve a grade B cleanliness environment.

After that, the third closing member 41 is closed by the operator's hands inserted in the gloves 13, and the open-close button 126 is then depressed by the operator to set the third closing member 41 to a locked state with the locking mechanism 123 so that the aseptic manipulation chamber 10 is hermetically isolated from the second operation chamber 32. Then, while a predetermined treatment is performed using the object M, the ventilation of the third ventilation mechanism for the aseptic manipulation chamber 10 continues so that a grade A cleanliness environment can be maintained in the aseptic manipulation chamber 10.

As described above, in the embodiment, after the object M is brought into the first operation chamber 31 from the outside, while the first operation chamber 31 is isolated from the outside it is ventilated such that the inside of the first operation chamber 31 returns to a grade C cleanliness environment. During this ventilation, the operator wipes off the object M to remove microbes adhering to its surface. The object M is then transferred to the second operation chamber 32, which is ventilated while being completely isolated from the first operation chamber 31 to return to a grade B cleanliness environment. During this ventilation, the operator wipes the object M with a decontaminant that is different from the decontaminant that was used in the first operation chamber 31, and microbes adhering to a surface of the object M are removed. When the ventilation of the second operation chamber 32 is completed, the object M is transferred to the aseptic manipulation chamber 10, which is maintained at a grade A cleanliness environment.

An operation in a decontamination mode of the embodiment is described below. As described above, in the ventilation mode, the object M is wiped off using a nonwoven fabric soaked in different decontaminants for the decontamination operations of the first and second operation chambers 31 and 32. This operation is carried out when the object M is affected by heat, such as a container in which cells or tissues are housed. Conversely, in the decontamination mode decontamination gas composed of hydrogen peroxide vapor acts upon the object M and the first operation chamber in the first decontamination operation for the first operation chamber 31; afterward, ventilation is carried out in the second decontamination operation for the second operation chamber 32 to remove any decontaminants remaining on the object M.

Namely, in the decontamination mode, step (1) is performed in a similar way as in the ventilation mode, in which the object M is introduced into the first operation chamber 31 through the inlet portion 36, and the first closing member 37 is closed to hermetically isolate the first operation chamber 31 from the outside. After that, in step (2) a decontamination operation is carried out for the object M housed in the first operation chamber 31 using hydrogen peroxide vapor generated in the evaporator 63 of the decontamination gas supply mechanism. At this time, the open-close valves 66 and 75 are open and the circulation blower 74 is actuated so that hydrogen peroxide vapor generated in the evaporator 63 is supplied to the first operation chamber 31 through the second branch passage 64b, and flows back to the evaporator 63 through the first branch passage 72a. At the same time, the air volume regulating valves 85 and 98 are closed and the air supply fan 51 and the air discharge fan 53 are stopped so that a positive pressure is maintained in the first operation chamber 31 and controlled by the open-close controls of the pressure-adjusting valves 70 and 78. The first operation chamber 31 is filled with hydrogen peroxide vapor, which acts on the object M, to remove microbes adhering to a surface of the object M and microbes adhering to an inner wall of the first operation chamber 31, which has been exposed to the external environment by opening the first closing member 37. During this operation, the control unit 120 maintains the locking mechanism 121 and 122 in the closed state, and the signal 127 is set to a lighting state to indicate that the first closing member 37 should remain in the closed state.

A ventilation procedure is carried out when a predetermined amount of hydrogen peroxide vapor has been supplied to the operation chamber 31. At this time, although the operation of the pump 62, which sends hydrogen peroxide vapor, is stopped, the open-close valves 66 and 75 are open and the circulation blower 74 is actuated to ventilate the pipes. On the other hand, the air volume regulating valves 85 and 95, which constitute the first ventilation mechanism, are opened by a predetermined degree and the air supply fan 51 and the air discharge fan 53 are actuated by a predetermined volume of air. Due to this, while air from the external environment of the aseptic manipulation system 100 flowing through the second gas supply passage 84 is purified by the HEPA filter 43 and supplied to the first operation chamber 31, gas containing hydrogen peroxide in the first operation chamber 31 passes through the second gas discharge passage 94, toxic substances contained in the gas are removed by the catalyst 96, and the gas is discharged to the outside of the aseptic manipulation system 100. This ventilation process is continued for a predetermined ventilation time during which the locking mechanisms 121 and 122 cannot be overridden and the closed states of the first closing member 37 and the second closing member 39 are maintained.

When a predetermined ventilation time has passed, the process proceeds to step (3), in which the signal 127 is changed to a lighting state to indicate that the second closing member 39 can be opened. Although operations after step (3) are the same as those of the ventilation mode, in step (5) the wiping-off operation of the object M in the second operation chamber 32 is not performed and instead, aeration is carried out for a predetermined time, in which residual decontaminants remaining on the object M are removed by the ventilation. On the other hand, in the first operation chamber 31 aeration is carried out, in which residual decontaminants remaining in the first operation chamber 31 are removed by the ventilation. Note that, in the decontamination mode, since the inside of the first operation chamber 31 communicating with the external environment is decontaminated with decontamination gas to reach an aseptic condition, it is not necessary to ventilate either the first operation chamber 31 for more than the first specified number of times and or the second operation chamber 32 for more than the second specified number of times when the first operation chamber 31 is in communication with the second operation chamber 32, as in the ventilation mode.

In the embodiment as described above, the ventilation mode and the decontamination mode are provided, and a process for introducing an object can be selected from these modes. Namely, the object M is introduced into the aseptic manipulation chamber 10 in the ventilation mode when the object M is affected by heat, and the object M is introduced into the aseptic manipulation chamber 10 in the decontamination mode when decontamination gas can be used without causing problems.

The present disclosure relates to subject matter contained in Japanese Patent Application No. 2014-262748 (filed on Dec. 25, 2014) which is expressly incorporated herein, by reference, in its entirety.

The invention claimed is:

1. An aseptic manipulation system, comprising:
an aseptic manipulation chamber, an air pressure of which is positive compared to an ambient pressure, so that interior of the aseptic manipulation chamber is kept in an aseptic condition;
a series of decontamination chambers provided for removing microbes adhering to an object prior to the object being introduced into the aseptic manipulation chamber, the decontamination chambers including:
a first operation chamber provided with an inlet portion that can be closed,
a second operation chamber connected to the first operation chamber and the aseptic manipulation chamber, a connecting portion to the aseptic manipulation chamber being provided with an outlet portion that can be closed,
a communication portion configured to facilitate communication between the first chamber and the second chamber, the communication portion being able to open and close,
an inlet portion door configured to open and close the inlet portion, an outlet portion door configured to open and close the outlet portion, and
a communication portion door configured to open and close the communication portion;
a first ventilation mechanism configured to ventilate interior of the first operation chamber, and to adjust an air pressure present in the interior of the first operation chamber by increasing or decreasing volume of air supplied to or discharged from the first operation chamber;
a second ventilation mechanism configured to ventilate interior of the second operation chamber, and to adjust an air pressure present in the interior of the second operation chamber by increasing or decreasing volume of air supplied to or discharged from the second operation chamber; and
a computer that is configured to monitor open-closed states of each of the inlet portion door, the outlet portion door, and the communication portion door, and is configured to control operations of the first ventilation mechanism and the second ventilation mechanism, wherein
the computer is configured to ventilate the interior of the first operation chamber with the first ventilation mechanism for more than a first specified number of times after an object is introduced into the first operation chamber from an outside environment and the inlet portion is closed while the communication portion is closed, and to ventilate the interior of the second operation chamber with the second ventilation mechanism for more than a second specified number of times, which is greater than the first specified number of times, after the object is transferred into the second operation chamber from the first chamber and the communication portion is closed while the outlet portion is closed,
the computer is configured to control the air pressures in the first and second operation chambers to be positive compared to the ambient pressure and less than the air pressure present in the interior of the aseptic manipulation chamber, and
each of the aseptic manipulation chamber and the decontamination chambers is provided with gloves installed therein, the gloves being accessible from an exterior of each of the aseptic manipulation chamber and the decontamination chambers.

2. The aseptic manipulation system according to claim 1, further comprising a locking mechanism configured to maintain the closed states of each of the inlet portion door, the outlet portion door, and the communication portion door, wherein
the computer is configured to control an operation of the locking mechanism to maintain the closed states of the inlet portion door and the communication portion door while ventilating the first operation chamber, and to maintain the closed states of the communication portion door and the outlet portion door while ventilating the second operation chamber.

3. The aseptic manipulation system according to claim 1, further comprising a decontamination gas supply device controlled by the computer to supply decontamination gas to the first operation chamber, wherein
the computer is configured to operate in a ventilation mode in which the first operation chamber, into which the object is introduced from the outside environment, is ventilated for more than the first specified number of times, and the second operation chamber, into which the object is transferred from the first operation chamber, is ventilated for more than the second specified number of times that is greater than the first specified number of times; and
in a decontamination mode in which the decontamination gas supply device supplies decontamination gas into the first operation chamber, into which the object is introduced from the outside environment, to decontaminate the object and the first operation chamber, and the first ventilation mechanism and the second ventilation mechanism ventilate the first operation chamber and the second operation chamber after the object is transferred from the operation chamber to the second operation chamber.

4. A method for introducing an object into an aseptic manipulation system comprising:
an aseptic manipulation chamber, the air pressure of which is positive compared to the ambient pressure, so that interior of the aseptic manipulation chamber is kept in an aseptic condition;
a series of decontamination chambers provided for removing microbes adhering to an object prior to the object being introduced into the aseptic manipulation chamber, the decontamination chambers including:
a first operation chamber provided with an inlet portion that can be closed,
a second operation chamber connected to the first operation chamber and the aseptic manipulation chamber, a connecting portion to the aseptic manipulation chamber being provided with an outlet portion that can be closed, and
a communication portion configured to facilitate communication between the first chamber and the second chamber, the communication portion being able to open and close;
a first ventilation mechanism configured to ventilate interior of the first operation chamber, and to adjust an air pressure present in the interior of the first operation chamber by increasing or decreasing volume of air supplied to or discharged from the first operation chamber; and
a second ventilation mechanism configured to ventilate interior of the second operation chamber, and to adjust an air pressure present in the interior of the second operation chamber by increasing or decreasing volume of air supplied to or discharged from the second operation chamber;
the method comprising:
opening the inlet portion while the communication portion is closed and ventilating the first operation chamber with the first ventilation mechanism for more than a first specified number of times after introducing the object into the first operation chamber from an outside environment and closing the inlet portion;
opening the communication portion while closing the outlet portion, and ventilating the second operation chamber with the second ventilation mechanism for more than a second specified number of times that is greater than the first specified number of times after transferring the object from the first operation chamber to the second operation chamber and closing the communication portion;
decontaminating the object in at least one of the first operation chamber and the second operation chamber being ventilated; and
opening the outlet portion to transfer the object from the second operation chamber to the aseptic manipulation chamber, wherein
the air pressures in the first and second operation chambers are maintained to be positive compared to the ambient pressure and less than the air pressure present in the interior of the aseptic manipulation chamber, and
each of the aseptic manipulation chamber and the decontamination chambers is provided with gloves installed therein, the gloves being accessible from an exterior of each of the aseptic manipulation chamber and the decontamination chambers.

5. The aseptic manipulation system according to claim 1, wherein the air pressure maintained in the second operation chamber is lower than the air pressure maintained in the first operation chamber, and the air pressure maintained in the aseptic manipulation chamber is higher than the air pressure maintained in the first operation chamber.

6. The aseptic manipulation system according to claim 1, wherein the aseptic manipulation chamber is disposed adjacent to the decontamination chambers.

7. The aseptic manipulation system according to claim 1, further comprising an indicator configured to signal completion of ventilation of the first operation chamber and the second operation chamber.

8. The method according to claim 4, wherein the object is decontaminated using a different decontamination medium in the first operation chamber and the second operation chamber.

9. The aseptic manipulation system according to claim 2, further comprising an indicator configured to signal completion of ventilation of the first operation chamber and the second operation chamber.

* * * * *